(12) United States Patent
Gliner (10) Patent No.: US 11,304,603 B2
(45) Date of Patent: Apr. 19, 2022

(54) ADVANCED CURRENT LOCATION (ACL) AUTOMATIC MAP ROTATION TO DETECT HOLES IN CURRENT POSITION MAP (CPM) MAPPING

(71) Applicant: Biosense Webster (Israel) Ltd., Yokneam (IL)

(72) Inventor: Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1277 days.

(21) Appl. No.: 15/681,474

(22) Filed: Aug. 21, 2017

(65) Prior Publication Data

US 2019/0053708 A1    Feb. 21, 2019

(51) Int. Cl.
*A61B 5/00* (2006.01)
*A61B 5/06* (2006.01)
(Continued)

(52) U.S. Cl.
CPC .......... *A61B 5/0044* (2013.01); *A61B 5/0538* (2013.01); *A61B 5/062* (2013.01); *A61B 5/063* (2013.01); *A61B 5/287* (2021.01); *A61B 5/316* (2021.01); *A61B 5/333* (2021.01); *A61M 25/0127* (2013.01); *G06F 16/56* (2019.01); *G06V 20/10* (2022.01); *A61B 5/6852* (2013.01);
(Continued)

(58) Field of Classification Search
CPC ....... G06T 17/20; G06T 17/205; G06T 19/20; G06T 15/40; A61B 2017/00053; A61B 5/742; A61B 5/6858; A61B 5/6859; A61B 90/37; A61B 2034/2072; A61B 2034/2053; A61B 2034/2051; A61B 2034/105; A61B 5/063; A61B 5/062; A61B 5/0538; A61B 5/287; A61B 5/0044; G06F 16/56

See application file for complete search history.

(56) References Cited

U.S. PATENT DOCUMENTS 5,687,737 A * 11/1997 Branham ............... A61B 5/287
                                                        600/509
6,226,542 B1    5/2001 Reisfeld
(Continued)

FOREIGN PATENT DOCUMENTS

EP           2837328 A1    2/2015

OTHER PUBLICATIONS

Extended European Search Report for corresponding European patent application No. 1819753.9, dated Feb. 4, 2019.
(Continued)

*Primary Examiner* — Amelie R Davis
*Assistant Examiner* — Helene Bor
(74) *Attorney, Agent, or Firm* — Notaro, Michalos & Zaccaria P.C.

(57) ABSTRACT

Catheterization is carried out by inserting a probe having a location sensor into a body cavity, and in response to multiple location measurements identifying respective mapped regions of the body cavity. Using the location measurements, a simulated 3-dimensional surface of the body cavity is constructed. One or more unmapped regions are delineated by rotating the simulated 3-dimensional surface about an axis. The simulated 3-dimensional surface of the body cavity is configured to indicate locations of the unmapped regions based on the location measurements.

21 Claims, 9 Drawing Sheets

(51) Int. Cl.
     *A61M 25/01*   (2006.01)
     *G06F 16/56*   (2019.01)
     *A61B 5/0538*  (2021.01)
     *A61B 5/287*   (2021.01)
     *A61B 5/316*   (2021.01)
     *A61B 5/333*   (2021.01)
     *G06V 20/10*   (2022.01)
     *A61M 25/06*   (2006.01)
     *A61B 17/00*   (2006.01)
     *A61B 34/20*   (2016.01)
     *G06T 17/20*   (2006.01)
     *A61B 34/10*   (2016.01)
     *A61B 90/00*   (2016.01)

(52) U.S. Cl.
     CPC .............. *A61B 5/742* (2013.01); *A61B 90/37* (2016.02); *A61B 2017/00053* (2013.01); *A61B 2017/00088* (2013.01); *A61B 2017/00092* (2013.01); *A61B 2034/105* (2016.02); *A61B 2034/2051* (2016.02); *A61B 2034/2053* (2016.02); *A61B 2034/2072* (2016.02); *A61M 2025/0166* (2013.01); *A61M 2025/0681* (2013.01); *G06T 17/20* (2013.01)

(56) References Cited

U.S. PATENT DOCUMENTS

| | | | |
|---|---|---|---|
| 6,301,496 | B1 | 10/2001 | Reisfeld |
| 6,814,733 | B2 | 11/2004 | Schwartz |
| 6,892,091 | B1 | 5/2005 | Ben Haim |
| 6,997,924 | B2 | 2/2006 | Schwartz |
| 7,156,816 | B2 | 1/2007 | Schwartz |
| 7,536,218 | B2 | 5/2009 | Govari |
| 7,756,576 | B2 | 7/2010 | Levin |
| 8,478,383 | B2 | 7/2013 | Bar-Tal |
| 2006/0173251 | A1 | 8/2006 | Govari |
| 2007/0016007 | A1 | 1/2007 | Govari |
| 2007/0038078 | A1 | 2/2007 | Osadchy |
| 2007/0049817 | A1* | 3/2007 | Preiss ............... A61B 8/4488 600/407 |
| 2008/0231640 | A1 | 9/2008 | Pighin |
| 2012/0184863 | A1* | 7/2012 | Harlev ............... A61B 5/349 600/509 |
| 2014/0088395 | A1* | 3/2014 | Dubois ............. A61B 18/1492 600/382 |
| 2014/0221803 | A1 | 8/2014 | Bar-Tal |
| 2015/0045647 | A1* | 2/2015 | Katz .................. A61B 5/283 600/409 |
| 2015/0164356 | A1 | 6/2015 | Merschon |
| 2015/0243080 | A1 | 8/2015 | Steinbach |
| 2015/0342662 | A1* | 12/2015 | Bustan ............... A61B 34/10 606/34 |
| 2016/0007852 | A1* | 1/2016 | Warner ............... A61B 6/465 600/374 |
| 2016/0247312 | A1* | 8/2016 | Santhanam ............. G06T 7/33 |
| 2017/0172455 | A1 | 6/2017 | Pressman |

OTHER PUBLICATIONS

Pratt, W.K. *Digital Image Processing*, John Wiley & Sons, Inc., New York, 4$^{th}$ edition, 2007, Chp. 18, pp. 633-648.

U.S. Appl. No. 15/351,972, filed Nov. 15, 2016.

* cited by examiner

ADVANCED CURRENT LOCATION (ACL) AUTOMATIC MAP ROTATION TO DETECT HOLES IN CURRENT POSITION MAP (CPM) MAPPING

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to instruments adapted for diagnosis of the heart. More particularly, this invention relates to current position mapping of an instrument inserted into the heart.

2. Description of the Related Art

The meanings of certain acronyms and abbreviations used herein are given in Table 1.

TABLE 1

Acronyms and Abbreviations

| ACL | Active Current Location |
|---|---|
| CPM | Current to Position Matrix |

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

U.S. Patent Application 2007/0016007, to Govari et al., whose disclosure is incorporated herein by reference, describes a hybrid magnetic-based and impedance-based position sensing system. The system includes a probe adapted to be introduced into a body cavity of a subject.

U.S. Patent Application Publication No. 2014/0221803 to Bar-Tal et al., whose disclosure is incorporated herein by reference discloses positioning body electrodes in galvanic contact with a body of a patient and positioning a mapping tool, having a mapping electrode, in a plurality of regions in the body. The method further includes tracking the mapping tool at different positions in each of the regions using a location-measuring system, and for each region, generating a respective set of calibration-currents between the body-electrodes and the mapping-electrode at the different positions in the region. A respective relation is derived for each region between the respective set of the calibration-currents and the different positions, and is used in determining the location of an investigation-tool in response to the different respective relations and investigation tool currents.

U.S. Patent Application Publication No. 2015/0045647 to Katz, whose disclosure is incorporated herein by reference, describes capturing, from an imaging system, a three-dimensional image of a body cavity, and using the captured 3-dimensional image to construct a simulated surface of the body cavity. A probe having a location sensor is inserted into the body cavity, and in response to multiple location measurements received from the location sensor, multiple positions are mapped within respective regions of the body cavity so as to generate respective mapped regions of the simulated surface. Based on the simulated surface and the respective mapped regions, one or more unmapped regions of the simulated surface are delineated, and the simulated surface of the body cavity is configured to indicate the delineated unmapped regions.

SUMMARY OF THE INVENTION

A CPM (current to position matrix) is used so that currents from an electrode of a catheter (with no magnetic sensor) can be used to track the catheter. The CPM is generated using a mapping catheter, with an electrode for measuring currents at a position, and a magnetic sensor for producing magnetic signals at the position. For a good CPM, it is important that the region of interest is well mapped, since the correspondence is non-linear, and extrapolation or interpolation of more than 1 or 2 mm becomes very inaccurate.

Embodiments of the invention rotate the map generated so as to display to the physician generating the map any "holes" or problems in the map's surface, causing the map to be not simply connected. The map itself is generated by first drawing a mesh between locational points found from the mapping catheter, and then filling the mesh with voxels to form a surface. It is this surface that is automatically rotated to show holes in the map, and these holes can then be filled by the physician so that the final surface has no holes, and is simply connected.

There is provided according to embodiments of the invention a method, which is carried out by inserting a probe having a location sensor into a body cavity, mapping multiple positions within respective regions of the body cavity. The method is further carried out in response to multiple location measurements received from the location sensor, so as to generate respective mapped regions of the body cavity, constructing, using the location measurements, a simulated 3-dimensional surface of the body cavity, delineating, by rotating the simulated 3-dimensional surface about an axis, one or more unmapped regions of the simulated 3-dimensional surface, and configuring the simulated 3-dimensional surface of the body cavity to indicate locations of the unmapped regions based on the location measurements.

In one aspect of the method delineating unmapped areas is performed by constructing simulated rays directed toward the simulated 3-dimensional surface, and identifying spatial regions wherein the rays fail to intersect the simulated 3-dimensional surface.

According to a further aspect of the method, identifying spatial regions is performed by graphically representing the rays that fail to intersect the simulated 3-dimensional surface on a 2-dimensional projection thereof.

According to yet another aspect of the method, configuring the simulated 3-dimensional surface includes varying an angle of rotation of the simulated 3-dimensional surface relative to a direction of the rays.

According to an additional aspect of the method, varying an angle of rotation includes rotating the simulated 3-dimensional surface about a center of mass thereof, while maintaining the direction of the rays.

According to another aspect of the method, varying an angle of rotation includes varying the direction of the rays while maintaining a position of the simulated 3-dimensional surface.

According to still another aspect of the method, the location sensor is a component of an active current location tracking system.

There is further provided according to embodiments of the invention an apparatus, including a probe configured for insertion into a body cavity of a patient, a location sensor in the probe for measuring a position of a distal end of the probe inside the body cavity, and a processor. The processor is configured for capturing, from an imaging system, a three-dimensional image of the body cavity, constructing, using the captured 3-dimensional image, a simulated 3-dimensional surface of the body cavity. The processor is further configured for mapping, while the probe is within the body cavity, multiple positions within respective regions of the body cavity in response to multiple location measurements received from the location sensor so as to generate respective mapped regions of the simulated 3-dimensional surface. The processor is further configured for delineating, by rotating the simulated 3-dimensional surface, one or more unmapped regions of the simulated 3-dimensional surface, and configuring the simulated 3-dimensional surface to indicate locations of the unmapped regions based on the location measurements.

There is further provided according to embodiments of the invention a computer software product operated in conjunction with a probe having a location sensor and adapted for insertion into a body cavity. The software product comprises a non-transitory computer-readable storage medium in which computer program instructions are stored, which instructions, when executed by a computer, cause the computer to perform the steps of: mapping multiple positions within respective regions of the body cavity, in response to multiple location measurements received from the location sensor, so as to generate respective mapped regions of the body cavity; constructing, using the location measurements, a simulated 3-dimensional surface of the body cavity; delineating, by rotating the simulated 3-dimensional surface about an axis, one or more unmapped regions of the simulated 3-dimensional surface; and configuring the simulated 3-dimensional surface of the body cavity to indicate locations of the unmapped regions based on the location measurements.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview.

Figure 1:
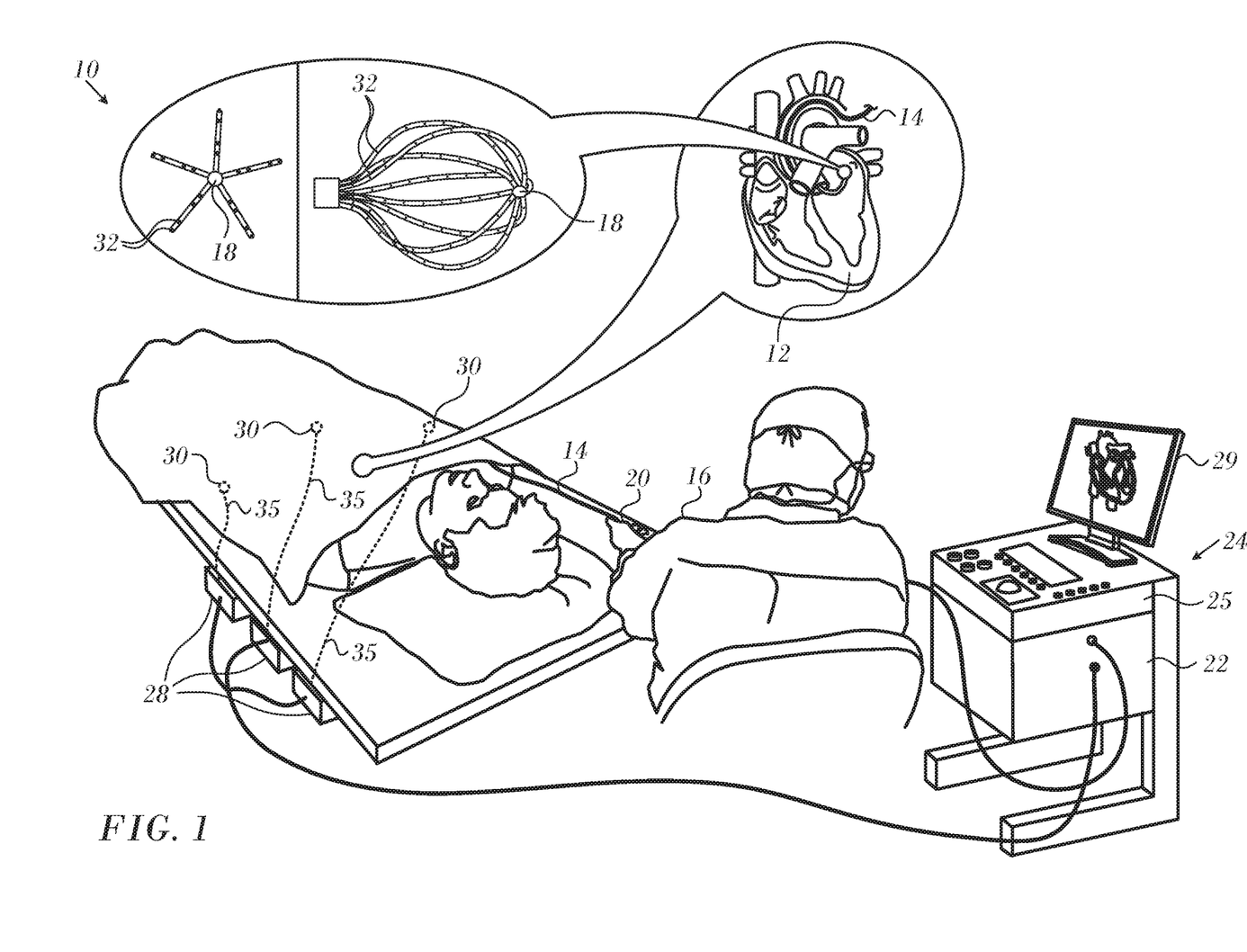
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a balloon or basket catheter as shown in the right portion of balloon 37, or a spline catheter as shown in the left portion. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with active current location (ACL) patches 30 and other components of a positioning sub-system for measuring location and orientation coordinates of the catheter 14. The processor 22, or another processor (not shown) may be an element of the positioning subsystem. The electrodes 32 and the body surface patches 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images.

Figure 2:
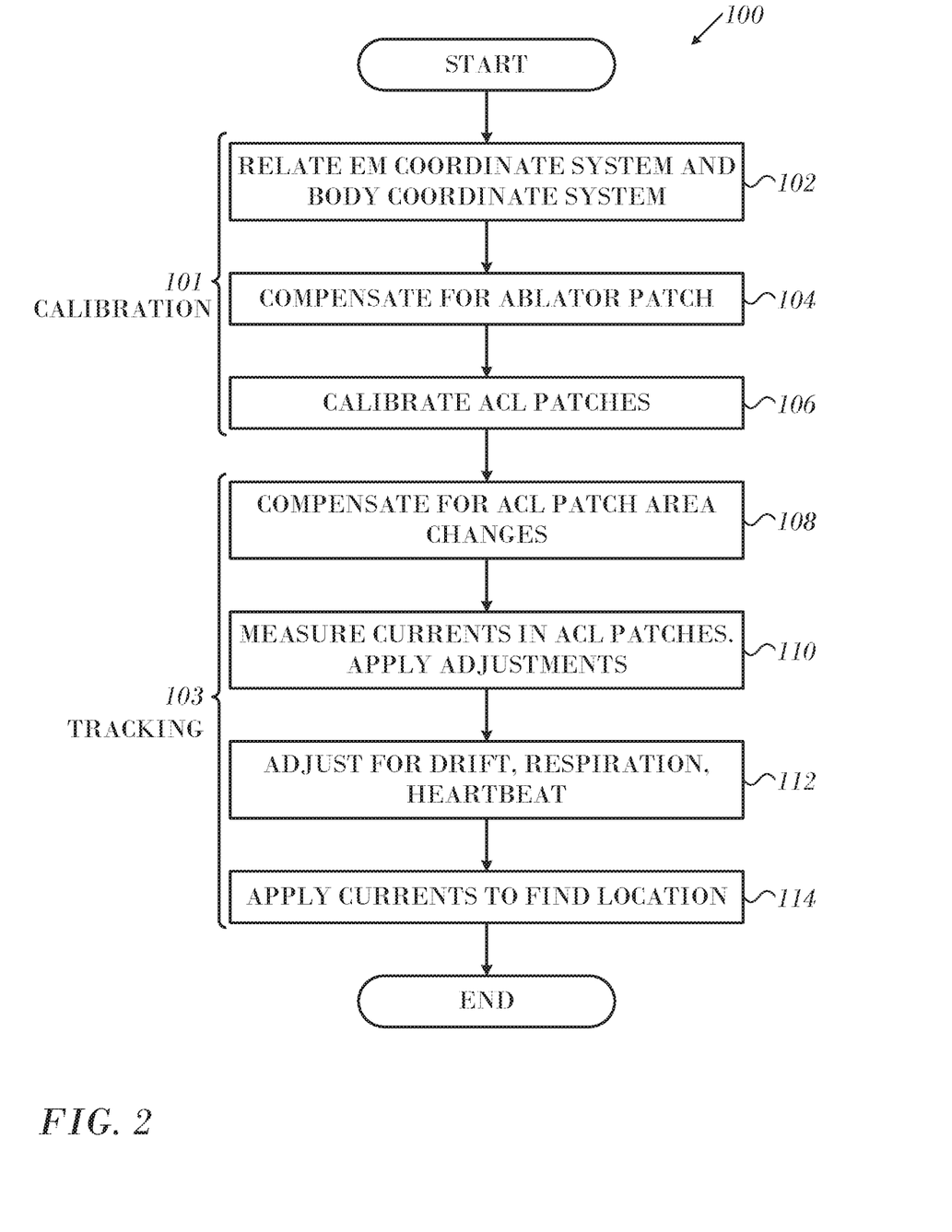
FIG. 2 is a flow chart schematically illustrating a process for operating the system shown in FIG. 1 in accordance with an embodiment of the invention.
Figure 3:
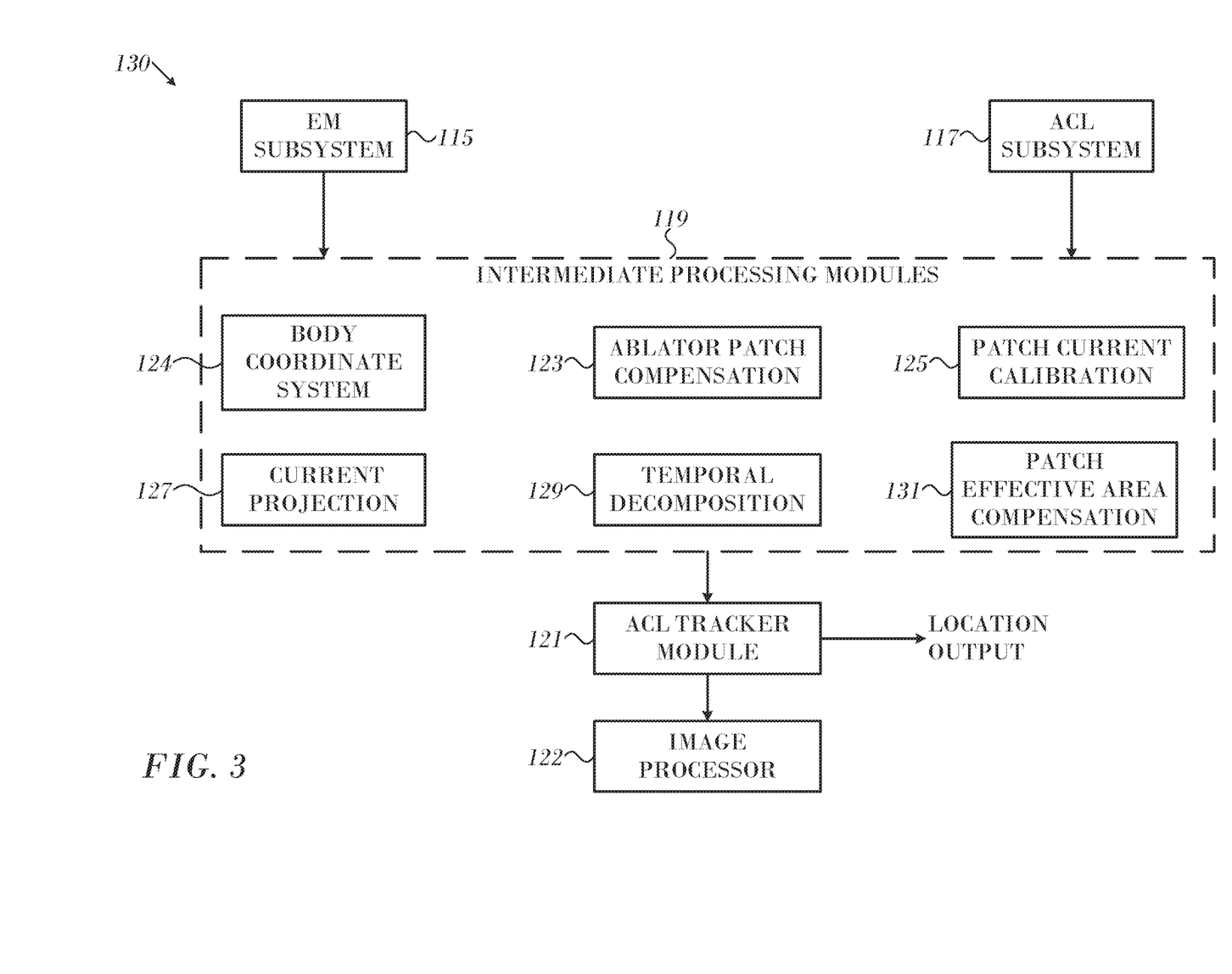
FIG. 3 is a simplified block diagram of the system shown in FIG. 1, according to an embodiment of the present invention in accordance with an embodiment of the invention.

FIG. 2 is a flow chart 100 schematically illustrating a process for operating system 10 (FIG. 1), and FIG. 3 is a simplified block diagram of the system 10, according to an embodiment of the present invention. To operate system 10, operator 16, or another operator of the system, first operates the system in a calibration phase 101, after which the system is operated in a tracking phase 103. Actions performed in each of the steps of the two phases are described in detail below. As is also described below, some of the actions may be performed in either phase.

In a reference frame correlation step 102, coordinates measured in an EM reference frame and in an active current location (ACL) reference frame are correlated. An EM tracker sub-system 115 generates measurements in the EM reference frame; an ACL tracker sub-system 117 generates measurements in the ACL frame, also herein termed the Body Coordinate System. The EM tracker sub-system measures locations using the electromagnetic fields generated by coils 28. The ACL tracker measures locations using currents through ACL patches 30.

Except where otherwise indicated, the following steps of the flowchart are performed in intermediate processing modules 119, which comprise ablator patch compensation module 123, body coordinate system module 124, patch current calibration module 125, current projection module 127, temporal decomposition module 129, and patch effective area compensation module 131.

In an ablator patch compensation step 104, processor performs measurements to determine how measured currents through the ACL patches may be compensated for because of current diversion through the ablator patch processor 130 performs the measurements by generating currents in the ablator patch and/or the ACL patches.

In an ACL patch calibration step 106, processor 130, using similar currents to those used for step 104, determines differences in individual ACL patch impedances. The differences in the impedances affect the currents in the ACL patches that are measured by the processor.

In a patch compensation step 108 processor 130 compensates for changes in the ACL patches effective area. The changes are typically caused by factors such as change of conductivity of the patch, usually because of sweating, and partial peeling of the patch from the skin of the patient.

Processor 130 uses currents similar to those generated in steps 104, 106 to determine compensation factors.

In a current projection step 110, the processor measures the currents in the ACL patches that are generated by currents injected into catheters being tracked, and applies the adjustments determined in steps 104, 106, 108 to the currents.

In a temporal adjustment step 112, the processor compensates for changes in the currents caused by three temporal factors: drift, respiration, and heartbeat. The compensation is implemented by applying different filters to the currents measured in step 110.

A final ACL step 114 comprises an initial training phase, wherein the processor stores current data and location data from the above steps and generates matrices relating the current and location data. ACL step 114 is performed in ACL tracker module 121. Once sufficient data has been obtained, processor 246 applies the generated matrices to the current data from step 112, to calculate the location for electrodes on catheter 14 (FIG. 1). The processor generates respective matrices for different "clusters," or regions, of the heart to improve the accuracy of current location. Output of the ACL tracker module 121 is linked to image processor 122 and the EM tracker sub-system 115, which is configured to construct a 3-dimensional model of a surface based on the locations of the catheter electrodes.

Figure 4:
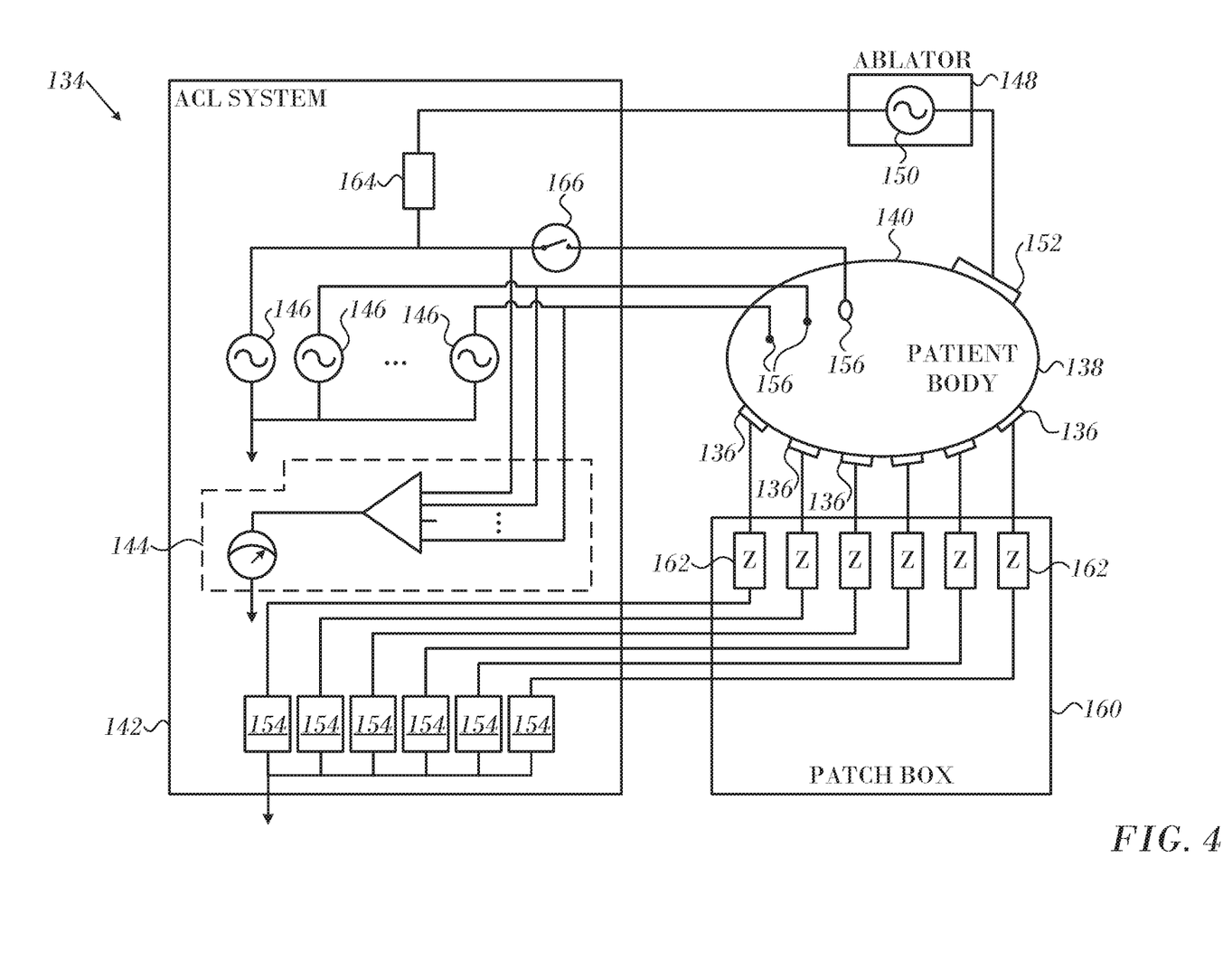
FIG. 4 is a schematic diagram of an ablation and active current location circuit for use with the system shown in FIG. 1 in accordance with an embodiment of the invention.

Reference is now made to FIG. 4, which is a schematic diagram of an ablation and active current location (ACL) circuit 134 for use with the system shown in FIG. 1. This arrangement is similar to that described in U.S. Patent Application Publications 2006/0173251, to Govari et al., and 2007/0038078, to Osadchy, which are herein incorporated by reference. The arrangement can be modified to operate in accordance with the principles of the present invention. A brief description follows for convenience of presentation.

A plurality of body surface electrodes 136, which can be adhesive skin patches, are coupled to a body surface 138 (e.g., the skin) of subject 140. The body surface electrodes 136 are sometimes referred to herein as "patches". In cardiac applications the body surface electrodes 136 are usually distributed so as to surround the heart, three on the chest of the subject and three on the back. However, the number of the body surface electrodes 136 is not critical, and they may be placed at convenient locations on the body surface 138 in the general vicinity of the site of the medical procedure.

A control unit 142, normally disposed in the console 24 (FIG. 1), includes current measurement circuitry 144 and one or more catheter electrode transmitters 146 for driving a current through one or more of the electrodes 136 to one or more of the body surface electrodes 136 at respective working frequencies. The control unit 142 is linked to a positioning processor. The control unit 142 is linked to an ablator 148, which comprises at least one ablation generator 150. Currents through the body surface electrodes 136 and an ablator body surface electrode 152 flow in a circuit with the ablation generator 150 and are measured by respective current measurement circuits that are disposed within body electrode receivers 154, sometimes referred to herein as "patch measurement circuits". The body electrode receivers 154 are typically incorporated in the control unit 142. Alternatively, they may be affixed to the body surface electrodes 136. Catheter electrodes are represented in FIG. 4 as measurement electrodes 156 (circles) and a dual-purpose electrode 158 (ellipse). The dual-purpose electrode 158 functions as an ablation electrode and also serves as one of the measurement electrodes.

The body surface electrodes 136 are connected to the body electrode receivers 154 via a patch box 160, which protects the system from ablation and defibrillation currents. Typically the system is configured with six body electrode receivers 154. The patch box parasitic impedances 162 (Z), are measured during production and thus known a priori. These impedances are discussed below.

Typically, although only two measurement electrodes 156 are shown for convenience, about 80 measurement electrodes are used for impedance measurements. Typically there are one or two ablation electrodes. The coordinates of a catheter inside the body are determined in the positioning system by passing currents between electrodes on the catheter and the body surface electrodes 136.

The control unit 142 may also control an ablation circuit, comprising ablator 148, and the dual-purpose electrode 158. The ablator 148 is typically disposed externally to the control unit 142 and incorporates the ablation generator 150. It connects with the ablator body surface electrode 152 and to an ablator filter 164, which in this example is shown within the control unit 142. However this location is not essential. A switch 166 configures the ablator circuit for different modes of operation as described below. Voltage measurement circuitry is provided for determining the output of the catheter electrode transmitters 146. It will be noted from inspection of FIG. 4 that the ablation circuit is connected to one of the catheter electrode transmitters 146.

3-Dimensional Model.

In the discussion that follows, spatial elements in a 3-dimensional model are sometimes referred to as voxels. However it will be understood that the principles of the invention are equally applicable to other 3-dimensional volumetric structures known in the art, such as various polygons, spheres, or 4-dimensional doxels. Moreover, in some embodiments the dimensions of a spatial element may be no larger than the height and width dimensions at the graphical resolution of a display monitor for the map, i.e., the dimensions of a 2-dimensional pixel.

Figure 5:
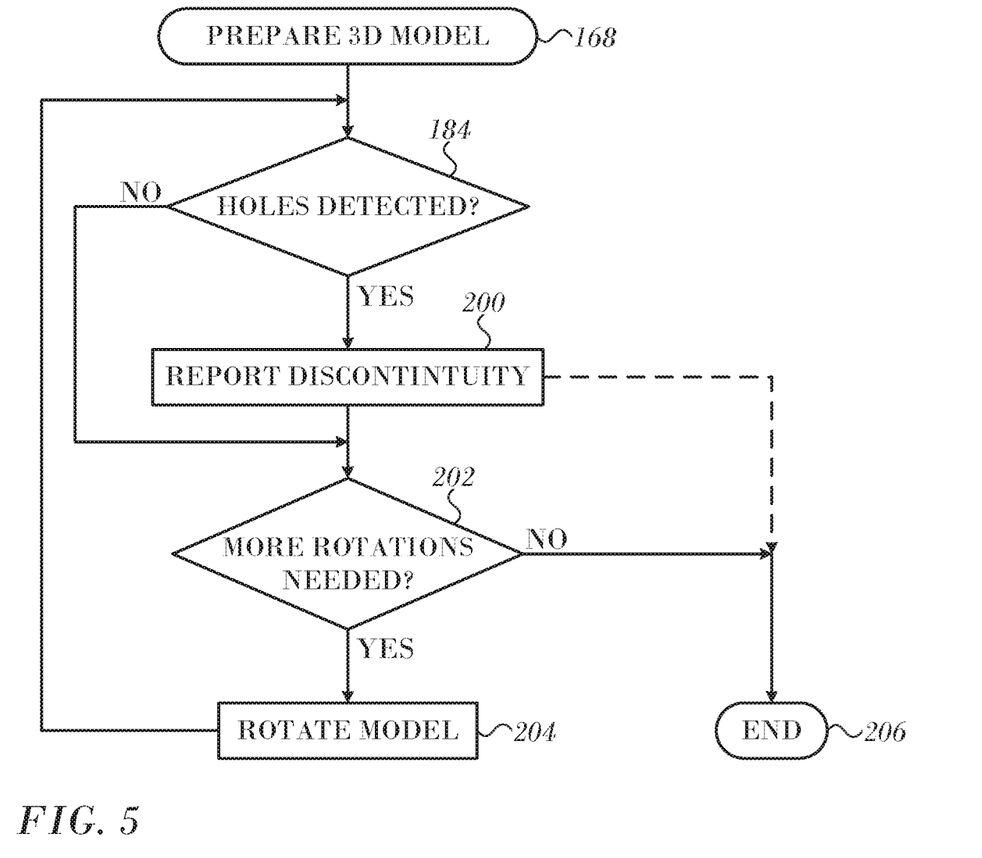
FIG. 5 is a flow chart of a method for displaying the quality of a current position map in accordance with an embodiment of the invention.

Reference is now made to FIG. 5, which is a flow chart of a method for displaying the quality of a current position map in accordance with an embodiment of the invention. The process steps are shown in a particular linear sequence for clarity of presentation. However, it will be evident that many of them can be performed in parallel, asynchronously, or in different orders. For example rotations are indicated as discrete steps, but may be performed continuously. Those skilled in the art will also appreciate that a process could alternatively be represented as a number of interrelated states or events, e.g., in a state diagram. Moreover, not all illustrated process steps may be required to implement the method.

The CPM is generated using a mapping catheter, with an electrode (giving currents at a position) and a magnetic sensor (giving magnetic signals at the position). At initial step 168 the heart is catheterized conventionally, typically with a multi-electrode mapping catheter, current readings taken, and a 3-dimensional model prepared using an imaging system. A suitable 3-dimensional model for this purpose is a triangular mesh, and can be prepared using the teachings of commonly assigned U.S. Patent Application Publication No. 2015/0164356, entitled Dynamic Feature Rich Anatomical Reconstruction from a Point Cloud, which is herein incorporated by reference. Values of data in the spatial elements, e.g., voxels that lie between the measured points may be interpolated by any of the above-described methods or other suitable interpolation techniques. In the following steps of the procedure, the spatial elements of the model that include a surface, such as the surface of the heart are individually characterized as being within a dense or sparse area of measured points. A CPM is prepared from the model, The values on such a map may be displayed in pseudocolors, and the sparse and dense zones graphically distinguished as taught in commonly assigned U.S. patent application Ser. No. 15/351,972 by Katz et al., entitled Marking Sparse Areas on Maps, whose disclosure is herein incorporated by reference.

Figure 6:
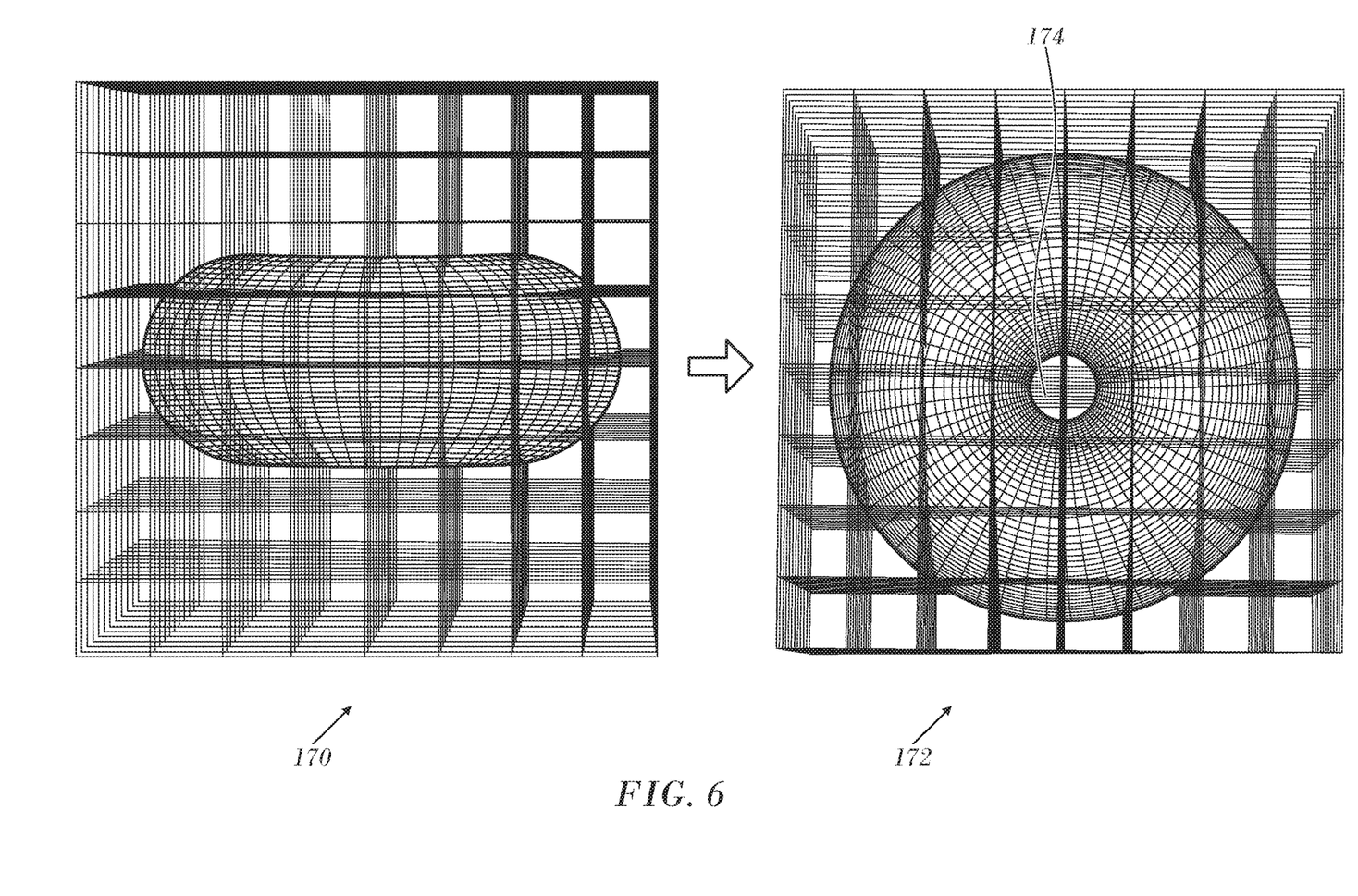
FIG. 6 is a set of two images of an idealized 3-dimensional model in accordance with an embodiment of the invention.

Reference is now made to FIG. 6, which is a set of two images of an idealized 3-dimensional model, i.e., a simulated 3-dimensional surface that is constructed from current readings obtained in initial step 168 (FIG. 5), in accordance with an embodiment of the invention. In image 170 is oblate, and apparently solid. However when rotated 90 degrees to produce image 172, it is apparent that the model is toroidal, with an unmapped central area 174. The central area 174 requires further mapping.

Figure 7:
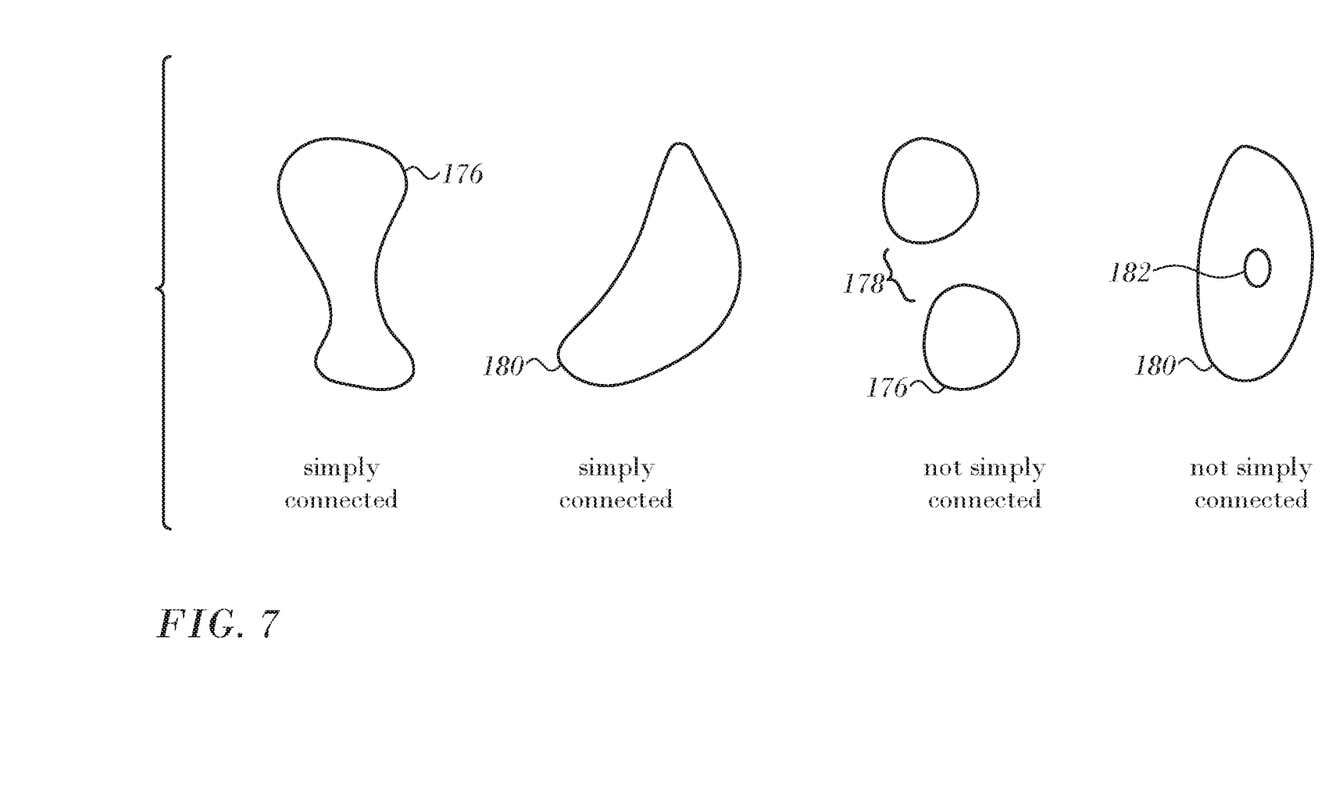
FIG. 7 is a set of 2-dimensional projections of a 3-dimensional model of a CPM, in accordance with an embodiment of the invention.

Reference is now made to FIG. 7, which is a set of 2-dimensional projections of a 3-dimensional model of a CPM, in accordance with an embodiment of the invention. When region 176, which appears solidly connected, is rotated, it becomes evident that a void 178 has not been adequately mapped. Similarly region 180 has a central unmapped void 182.

Figure 8:
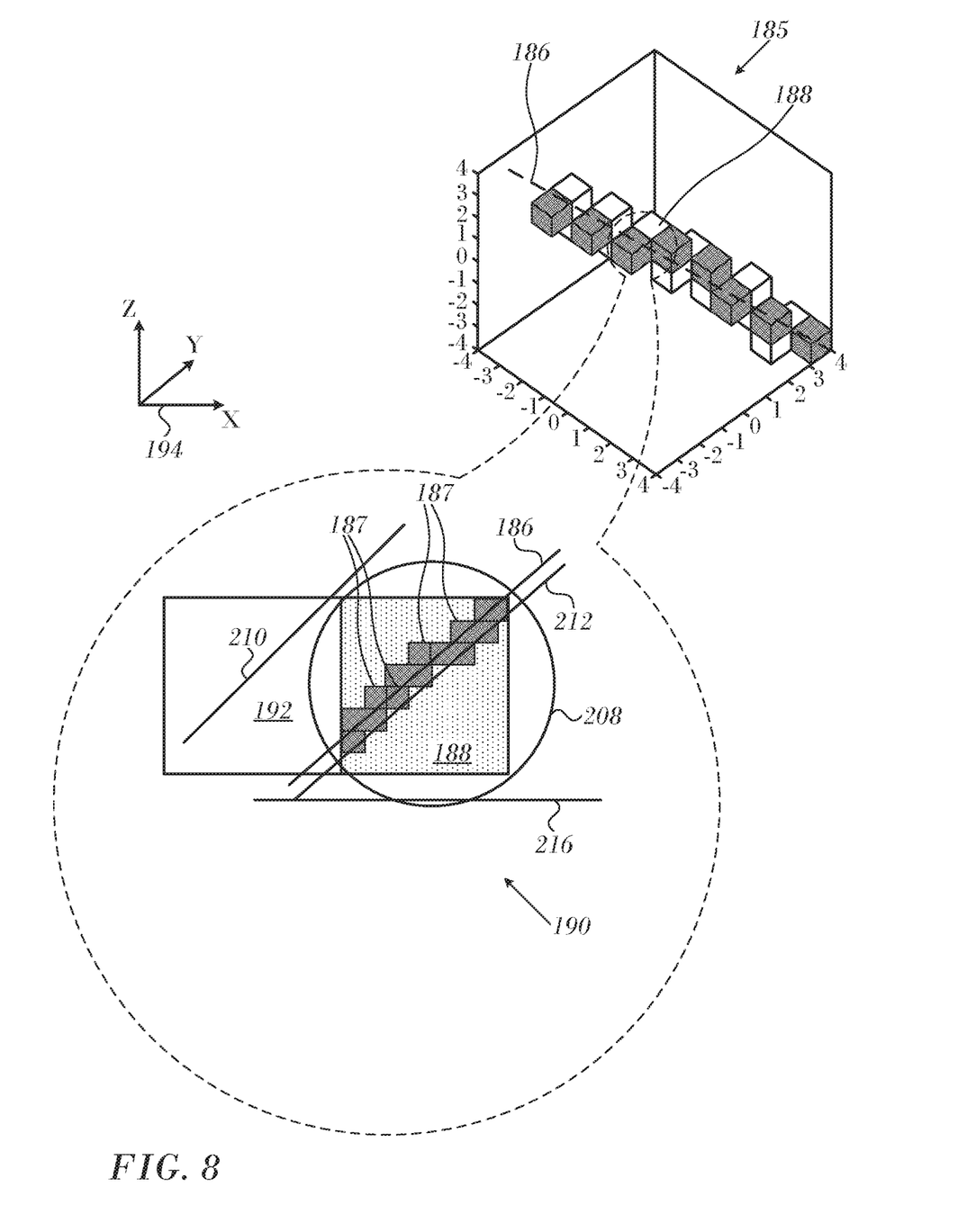
FIG. 8 is a set of diagrams illustrating a virtual ray that is directed through a grid of voxels in a 3-dimensional model in accordance with an embodiment of the invention.

Reverting to FIG. 5, at decision step 184, it is determined if voids in the model are present. This step is carried out by defining the edges of the model using conventional edge detection algorithms and then checking for discontinuities in the interior of the model. Virtual rays are defined as shown in FIG. 8, which is a set of diagrams illustrating virtual rays that are directed through a 3-dimensional grid 185 of voxels, including voxel 188 comprising a 3-dimensional model in accordance with an embodiment of the invention. Voxel 188 includes a portion of the simulated surface 187 of the 3-dimensional model. The balloon in the lower portion of the figure shows a 2-dimensional projection 190 of the voxel 188 with reference to 3-dimensional coordinate system 194.

A voxel represents a value in a regular grid in 3-dimensional space. However, for purposes of this discussion, and for convenience of computation, a ray is considered to pass through a voxel if the ray passes through a sphere that circumscribes the voxel. The circumscribing sphere typically has a radius of 1 mm.

Listing 1

Define parallel vectors of the following form in any direction
$\vec{Y}_l = ax + by + c_i$
Function _Void
{
    For each voxel v through which $\vec{Y}_l$ passes
        If v is empty (does not include the simulated surface) then
            Set is_hole = true Listing 1
-continued     Else
        set is_hole = false
        return not_void
    next voxel v
    return void
}

Application of the function shown in Listing 1 is illustrated by projection 190, in which the sphere circumscribing the voxel 188 is indicated by a circle 208. For the voxel 188 the function in Listing 1 would return "not_void" in the case of virtual ray 186 and virtual ray 212, as they pass through the circle 208 and intersect the surface 187. Virtual ray 214 passes through the voxel 188, but does not intersect the surface 187. It would nevertheless return "not is_hole" because voxel 188 includes surface 187. Non parallel virtual ray 216 passes through the circle 208 but not the projection 190 of the voxel 188. Nevertheless, virtual ray 216 would also cause "not is_hole" to be returned.

Projection 190 includes voxel 192, which is adjacent to voxel 188 in the grid 185. Voxel 192 does not contain the surface 187. The function of Listing 1 would return "is_hole" in the case of virtual ray 210, which passes through voxel 192, but never intersects the circle 208.

Figure 9:
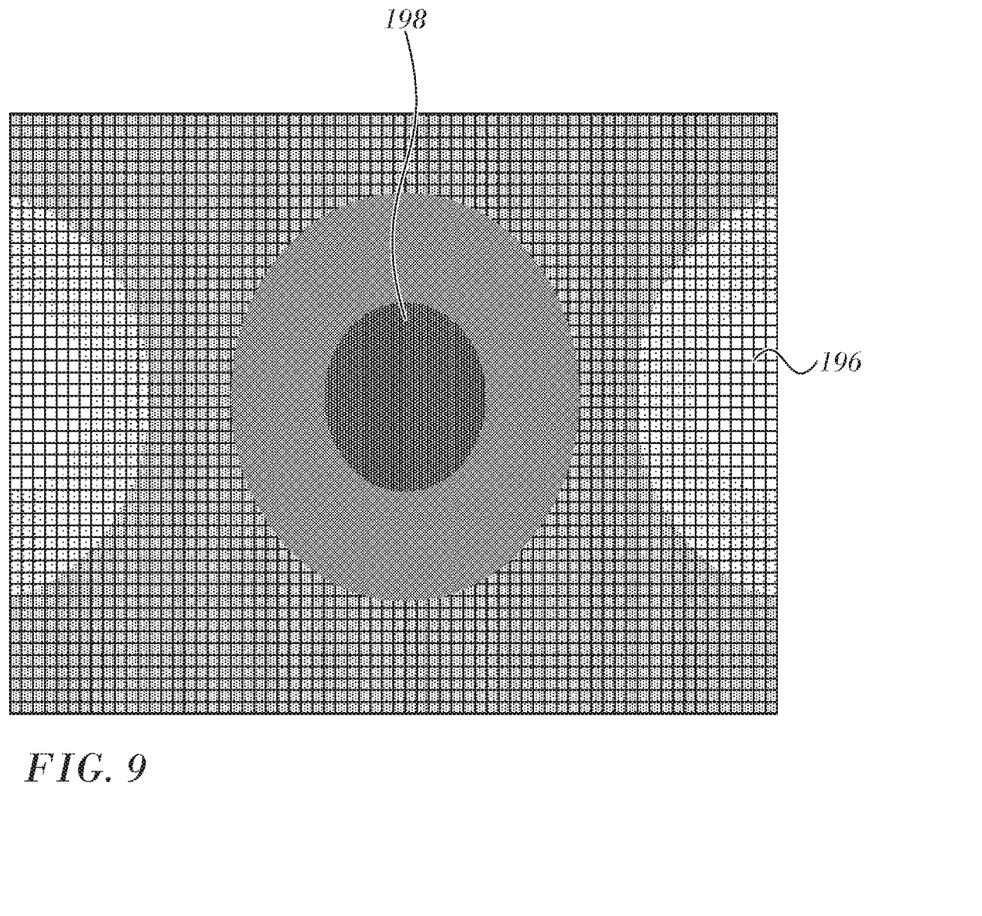
FIG. 9 is a projection map in accordance with an embodiment of the invention.

If for any ray, the function returns "not is_hole", a void is excluded, and no other voxels need be examined with respect to that ray. When such a ray passes through a voxel occupied by the simulated surface of the 3-dimensional model, the ray is considered to be interrupted, and the intersection of the ray and the voxel is detected by the image processor. A ray passing through a void in the 3-dimensional model can be represented on a projection map, such as map 196 shown in FIG. 9, in which a hatched area 198 corresponding to the color "blue" represents failure of the rays to intersect the voxels occupied by the simulated surface of the 3-dimensional model. The area 198 therefore represents a void, and would require additional mapping with the catheter. Spatial analysis of the map identifies the largest contiguous "blue" area, i.e., an area having a ray density value that is less than a predefined threshold, using known algorithms. Although the existence of a void in the 3-dimensional model is a binary decision based on each ray, shading in the map 196 provides a measure of the density of voids in the 3-dimensional model.

One algorithm that is suitable for rotation of the 3-dimensional model about a center of mass relies on discrete image functions to calculate spatial moments, and is disclosed in the text Pratt, William K., Digital Image Processing, New York, John Wiley & Sons, Inc., Fourth Edition, 2007, Chap. 18, (p. 633 et seq.), which is herein incorporated by reference. Those skilled in the art may configure the image processor 122 (FIG. 3) to execute this algorithm.

If the determination at decision step 184 is negative, then the model may need to be evaluated by changing the angle of rotation of the model relative to the virtual rays. Control proceeds to decision step 202, which is described below.

If the determination at decision step 184 is affirmative, then control proceeds to step 200. The discontinuity, its spatial location and extent are reported to the operator, who may then optionally proceed directly to final step 206 and navigate the catheter to supplement the mapping procedure in the area of the discontinuity.

Alternatively, the procedure may be iterated to define additional voids. At decision step 202, it is determined if more rotational maneuvers of the 3-dimensional model need to be carried out to fully evaluate the mapping. Rotations may be done along more than one axis to assure a complete examination of the model. For example in an arbitrary 3-dimensional coordinate system having x, y, and z axes, any of the axes may be chosen to rotate the model about its center of mass.

If the determination at decision step 202 is affirmative, then control proceeds to step 204 where the appropriate rotation is carried out. Control then returns to decision step 184.

If the determination at decision step 202 is negative, then the procedure terminates at step 206 as discussed above.

Alternate Embodiments

The previous embodiment develops projection maps, such as the map 196 (FIG. 9) by rotating the 3-dimensional model. Alternatively, the 3-dimensional model is held in a fixed position and the direction of the virtual rays varied to develop a series of projection maps. Changing the relative aspects of the model relative to the virtual rays may be accomplished by a combination of movements of the 3-dimensional model and variation in the direction of the virtual rays. Further alternatively it is also possible to simultaneously generate and analyze multiple projection maps by appropriate simultaneous or near-simultaneous generation of virtual rays in multiple directions.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
inserting a probe having a location sensor into a body cavity;
mapping multiple positions within respective regions of the body cavity, in response to multiple location measurements received from the location sensor, so as to generate respective mapped regions of the body cavity;
constructing, using the location measurements, a simulated 3-dimensional surface of the body cavity;
delineating, by rotating the simulated 3-dimensional surface about an axis, one or more unmapped regions of the simulated 3-dimensional surface; and
configuring the simulated 3-dimensional surface of the body cavity to indicate locations of the unmapped regions based on the location measurements,
wherein the method comprises the following steps, performed by a processor:
a reference frame correlation step, wherein coordinates measured in an electromagnetic reference frame and in an active current location reference frame are correlated, wherein an electromagnetic tracker subsystem generates measurements in the electromagnetic reference frame, an active current location tracker sub-system generates measurements in the active current location frame, wherein the electromagnetic tracker sub-system measures locations using electromagnetic fields generated by coils, wherein the active current location tracker measures locations using currents through active current location patches, an ablator patch compensation step, wherein the processor performs measurements to determine how measured currents through the active current location patches may be compensated for,
an active current location patch calibration step, wherein the processor determines differences in individual active current location patch impedances,
a patch compensation step, wherein the processor compensates for changes in effective areas of the active current location patches,
a current projection step, wherein the processor measures currents in the active current location patches that are generated by currents injected into the probe,
a temporal adjustment step, wherein the processor compensates for changes in the currents caused by factors selected from the group consisting of drift, respiration, and heartbeat,
a final active current location step, wherein the processor stores current data and location data from the reference frame correlation step, the ablator patch compensation step, the active current location patch calibration step, the patch compensation step, the current projection step and the temporal adjustment step and generates at least one matrix relating stored current and location data,
wherein the ablator patch compensation step, the active current location patch calibration step, the patch compensation step, the current projection step, the temporal adjustment step, and the final active current location step are performed in intermediate processing modules, which comprise an ablator patch compensation module, body coordinate system module, patch current calibration module, current projection module, temporal decomposition module, and patch effective area compensation module.

2. The method according to claim 1, wherein the step of delineating comprises:
constructing simulated rays directed toward the simulated 3-dimensional surface; and
identifying spatial regions wherein the rays fail to intersect the simulated 3-dimensional surface.

3. The method according to claim 2, wherein identifying spatial regions is performed by graphically representing the rays that fail to intersect the simulated 3-dimensional surface on a 2-dimensional projection thereof.

4. The method according to claim 2, wherein configuring the simulated 3-dimensional surface comprises varying an angle of rotation of the simulated 3-dimensional surface relative to a direction of the rays.

5. The method according to claim 4, wherein varying an angle of rotation comprises rotating the simulated 3-dimensional surface about a center of mass thereof, while maintaining the direction of the rays.

6. The method according to claim 4, wherein varying an angle of rotation comprises varying the direction of the rays while maintaining a position of the simulated 3-dimensional surface.

7. The method according to claim 1, wherein the location sensor is a component of an active current location tracking system.

8. An apparatus, comprising:
a probe, configured for insertion into a body cavity of a patient;
a location sensor in the probe for measuring a position of a distal end of the probe inside the body cavity; and a processor configured for:

capturing, from an imaging system, a three-dimensional image of the body cavity;

constructing, using the captured 3-dimensional image, a simulated 3-dimensional surface of the body cavity;

mapping, while the probe is within the body cavity, multiple positions within respective regions of the body cavity, in response to multiple location measurements received from the location sensor, so as to generate respective mapped regions of the simulated 3-dimensional surface;

delineating, by rotating the simulated 3-dimensional surface, one or more unmapped regions of the simulated 3-dimensional surface; and configuring the simulated 3-dimensional surface to indicate locations of the unmapped regions based on the location measurements, wherein the processor is configured to perform the following steps:

- a reference frame correlation step, wherein coordinates measured in an electromagnetic reference frame and in an active current location reference frame are correlated, wherein an electromagnetic tracker sub-system generates measurements in the electromagnetic reference frame, an active current location tracker sub-system generates measurements in the active current location frame, wherein the electromagnetic tracker sub-system measures locations using electromagnetic fields generated by coils, wherein the active current location tracker measures locations using currents through active current location patches,
- an ablator patch compensation step, wherein the processor performs measurements to determine how measured currents through the active current location patches may be compensated for,
- an active current location patch calibration step, wherein the processor determines differences in individual active current location patch impedances,
- a patch compensation step, wherein the processor compensates for changes in effective areas of the active current location patches,
- a current projection step, wherein the processor measures currents in the active current location patches that are generated by currents injected into the probe,
- a temporal adjustment step, wherein the processor compensates for changes in the currents caused by factors selected from the group consisting of drift, respiration, and heartbeat,
- a final active current location step, wherein the processor stores current data and location data from the reference frame correlation step, the ablator patch compensation step, the active current location patch calibration step, the patch compensation step, the current projection step and the temporal adjustment step and generates at least one matrix relating stored current and location data,
- wherein the ablator patch compensation step, the active current location patch calibration step, the patch compensation step, the current projection step, the temporal adjustment step, and the final active current location step are performed in intermediate processing modules, which comprise an ablator patch compensation module, body coordinate system module, patch current calibration module, current projection module, temporal decomposition module, and patch effective area compensation module.

9. The apparatus according to claim 8, wherein delineating comprises:

constructing simulated rays directed toward the simulated 3-dimensional surface; and identifying spatial regions wherein the rays fail to intersect the simulated 3-dimensional surface.

10. The apparatus according to claim 9, wherein the processor is configured for identifying spatial regions is performed by graphically representing a density of the rays that fail to intersect the simulated 3-dimensional surface on a 2-dimensional projection thereof.

11. The apparatus according to claim 9, wherein configuring the simulated 3-dimensional surface comprises varying an angle of rotation of the simulated 3-dimensional surface relative to a direction of the rays.

12. The apparatus according to claim 11, wherein varying an angle of rotation comprises rotating the simulated 3-dimensional surface about an axis while maintaining the direction of the rays.

13. The apparatus according to claim 11, wherein varying an angle of rotation comprises varying the direction of the rays while maintaining a position of the simulated 3-dimensional surface.

14. The apparatus according to claim 8, wherein the location sensor is a component of an active current location tracking system.

15. A computer software product operated in conjunction with a probe having a location sensor and adapted for insertion into a body cavity, the software product including a non-transitory computer-readable storage medium in which computer program instructions are stored, which instructions, when executed by a computer, cause the computer to perform the steps of:

mapping multiple positions within respective regions of the body cavity, in response to multiple location measurements received from the location sensor, so as to generate respective mapped regions of the body cavity;

constructing, using the location measurements, a simulated 3-dimensional surface of the body cavity;

delineating, by rotating the simulated 3-dimensional surface about an axis, one or more unmapped regions of the simulated 3-dimensional surface; and configuring the simulated 3-dimensional surface of the body cavity to indicate locations of the unmapped regions based on the location measurements, wherein the instructions further cause the computer to perform the steps of:

- a reference frame correlation step, wherein coordinates measured in an electromagnetic reference frame and in an active current location reference frame are correlated, wherein an electromagnetic tracker sub-system generates measurements in the electromagnetic reference frame, an active current location tracker sub-system generates measurements in the active current location frame, wherein the electromagnetic tracker sub-system measures locations using electromagnetic fields generated by coils, wherein the active current location tracker measures locations using currents through active current location patches,
- an ablator patch compensation step, wherein the processor performs measurements to determine how measured currents through the active current location patches may be compensated for,
- an active current location patch calibration step, wherein the processor determines differences in individual active current location patch impedances, a patch compensation step, wherein the processor compensates for changes in effective areas of the active current location patches, a current projection step, wherein the processor measures currents in the active current location patches that are generated by currents injected into the probe, a temporal adjustment step, wherein the processor compensates for changes in the currents caused by factors selected from the group consisting of drift, respiration, and heartbeat, a final active current location step, wherein the processor stores current data and location data from the reference frame correlation step, the ablator patch compensation step, the active current location patch calibration step, the patch compensation step, the current projection step and the temporal adjustment step and generates at least one matrix relating stored current and location data, wherein the ablator patch compensation step, the active current location patch calibration step, the patch compensation step, the current projection step, the temporal adjustment step, and the final active current location step are performed in intermediate processing modules, which comprise an ablator patch compensation module, body coordinate system module, patch current calibration module, current projection module, temporal decomposition module, and patch effective area compensation module.

16. The computer software product according to claim 15, wherein the step of delineating comprises:
constructing simulated rays directed toward the simulated 3-dimensional surface; and
identifying spatial regions wherein the rays fail to intersect the simulated 3-dimensional surface.

17. The computer software product according to claim 16, wherein identifying spatial regions is performed by graphically representing the rays that fail to intersect the simulated 3-dimensional surface on a 2-dimensional projection thereof.

18. The computer software product according to claim 16, wherein configuring the simulated 3-dimensional surface comprises varying an angle of rotation of the simulated 3-dimensional surface relative to a direction of the rays.

19. The computer software product according to claim 18, wherein varying an angle of rotation comprises rotating the simulated 3-dimensional surface about a center of mass thereof, while maintaining the direction of the rays.

20. The computer software product according to claim 18, wherein varying an angle of rotation comprises varying the direction of the rays while maintaining a position of the simulated 3-dimensional surface.

21. The computer software product according to claim 15, wherein the location sensor is a component of an active current location tracking system.

* * * * *